United States Patent
Cohen et al.

(10) Patent No.: US 6,515,130 B1
(45) Date of Patent: Feb. 4, 2003

(54) **PROCESS FOR PREPARING [S-(R*,S*)]-β-[[[1-[1-OXO-3(4-PIPERIDINYL)PROPYL]-3-PIPERIDINYL]CARBONYL]AMINO]-3-PYRIDINEPROPANOIC ACID AND DERIVATIVES**

(76) Inventors: Judith H. Cohen, 107 Citadel Ct., North Wales, PA (US) 19454; Michael Justus, Lindenplatz 12B, 8203 Schaffhausen (CH); Cynthia A. Maryanoff, P.O. Box 239, New Hope, PA (US) 18938; Armin Rössler, Ludwig-Gerer Str 9, 78250 Tengen (DE); Fridtjof Schröder, Im Grund 14, CH - 8442 Hettlingen (CH); Kirk L. Sorgi, 2543 Red Gate Dr., Doylestown, PA (US) 18901; Frank J. Villani, Jr., 2 Pinewood La., Perkasie, PA (US) 18944; Christian Weh, Griesstrasse 4, 78266 Büsingen (DE)

( * ) Notice: Subject to any disclaimer, the term of this patent is extended or adjusted under 35 U.S.C. 154(b) by 0 days.

(21) Appl. No.: 09/532,375

(22) Filed: Mar. 21, 2000

Related U.S. Application Data

(60) Provisional application No. 60/125,671, filed on Mar. 22, 1999.

(51) Int. Cl.⁷ ..................... C07D 401/12; A61K 31/445
(52) U.S. Cl. ...................... 546/187; 546/189; 514/314; 514/316
(58) Field of Search ................................ 514/316, 314; 546/187, 189

(56) References Cited

U.S. PATENT DOCUMENTS

| | | | |
|---|---|---|---|
| 4,585,887 A | 4/1986 | Jolidon et al. | 560/38 |
| 5,254,573 A | 10/1993 | Bovy et al. | 514/357 |
| 5,840,961 A | 11/1998 | Behling et al. | 560/172 |

FOREIGN PATENT DOCUMENTS

| | | | |
|---|---|---|---|
| WO | WO 95/08536 | 3/1995 | C07D/211/60 |
| WO | WO 97/41102 | 11/1997 | C07D/211/60 |
| WO | WO98/02410 | 1/1998 | C07C/227/32 |

OTHER PUBLICATIONS

Hoekstra et al. "Solid phase parallel synthesis applied to . . . " Bioorg. Med. Chem. Let. v.6, 2371–2376 (1996).*

J.G. Rico, R.J. Lindmark, T.E. Rogers, & P.R. Bovy, A Highly Stereoselective Michael Addition to an a,β–Unsaturated Ester as the Crucial Step in the Synthesis of a Novel β–Amino Acid–Containing Fibrinogen Receptor Antagonist, J. Org. Chem. 1993, 58,7948–7951.

F.A. Davis, J.M. Szewczyk & R.E. Reddy, An Efficient Synthesis of (S)—(+) –Ethyl β–Amino–3–pyridinepropanoate Using Enantiopure Sulfinimines, J. Org. Chem. 1996, 61, 2222–2225.

T.P. Tang & J.A. Ellman, The tert–Butanesulfinyl Group: An Ideal Chiral Directing Group and Boc–Surrogate for the Asymmetric Synthesis and Applications of β–Amino Acids, J. Org. Chem. 1999, 64, 12–13.

M.A. Croucher, B.S. Meldrum, & P. Krogsgaard–Larsen, Anticonvulsant Activity of GABA Uptake Inhibitors and Their Prodrugs Following Central or Systemic Administration, European Journal of Pharmacology, 89 (1983) 217–228.

D.L. Lee, C.J. Morrow, & H. Rapport, α–Methylenelactam Rearrangement, J. Org. Chem., vol. 39, No. 7, 1974, 893–902.

N.J. Leonard & D. Choudhur, γ–Pyrones by Isomerization. Substituted 3,5–Dibenzyl–4H–pyran–4–ones, Noyes Chemical Laboratory, University of Illinois, vol. 79, (1957) 156–160.

Akkerman, A.M., De Jong, D.K. and Vaeldstra, H., Synthetic Oxytocics. 1. 3–(Piperidyl–(N)–Methyl)–Indoles and Related Compounds, Rec. Trav. Chim Pays–Bas, 1951, 70 p. 8899–916.

William J. Hoekstra et al., Solid–Phase Parallel Synthesis Applied to Lead Optimization: Discovery of Potent Analogues of the GPIIb/IIIa Antagonist RWJ–50042, Bioorganic Medical Chemistry Letters, vol. 6, no. 20, 1996, pp. 2371–2376.

William J. Hoekstra et al., Solid Phase Synthesis Via N–Terminal Attachment to the 2–Chlorotrityl Resin, Tetrahedron Letters, vol. 38, no. 15, 1997, pp. 2629–2632.

* cited by examiner

*Primary Examiner*—Alan L. Rotman

(57) ABSTRACT

A process for preparing a compound of formula I

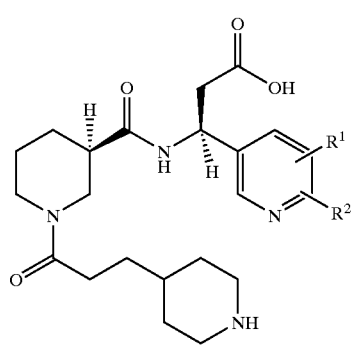

wherein $R^1$ and $R^2$ are independently selected from the group consisting of hydrogen, lower alkyl and halogen

19 Claims, No Drawings

PROCESS FOR PREPARING [S-(R*,S*)]-β-[[[1-[1-OXO-3(4-PIPERIDINYL)PROPYL]-3-PIPERIDINYL]CARBONYL]AMINO]-3-PYRIDINEPROPANOIC ACID AND DERIVATIVES

CROSS REFERENCE TO RELATED APPLICATIONS

This application claims benefit to U.S. Provisional Application No. 60/125,671, filed on Mar. 22, 1999.

BACKGROUND OF THE INVENTION

Field of the Invention

The invention relates to a process of preparing [S-(R*, S*)]-β-[[[1-[1-oxo-3-(4-piperidinyl)propyl]-3-piperidinyl]carbonyl]amino]-3-pyridinepropanoic acid derivatives represented by the formula

I

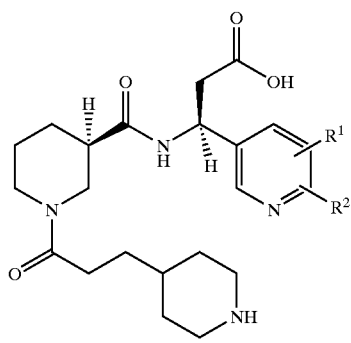

wherein $R^1$ and $R^2$ are independently selected from hydrogen, lower alkyl and halogen.

The compounds of formula I and method of making and using the compounds of formula I are described in WO 97/41102, Nov. 6, 1997.

Compounds of formula I are antagonists of the platelet fibrinogen receptor (GP 11b/111a antagonist). Thus, the compounds of formula I are useful for the treatment of thrombotic disorders such as restenosis post-angioplasty, unstable/stable angina and myocardial infarction.

A known method of the preparation of a compound of formula I is disclosed in WO 97/41102 involving coupling of enantiomerically enriched methyl (S)-3-amino-3-pyridylpropanoate with N-(t-butoxycarbonyl)-(R)-nipecotic acid followed by removal of the N-t-butoxycarbonyl protecting group under acidic conditions and coupling with 3-(N-t-butoxycarbonyl-4-piperidyl)propionic acid. The crude ester product is then hydrolyzed using aqueous LiOH and the N-t-butoxycarbonyl amino protecting group is removed under acidic conditions with trifluoroacetic acid ("TFA"). The bis-TFA salt is isolated as a white amorphous solid.

A process for preparing N-(3-piperidinyl carbonyl)-β-alanine derivatives is disclosed in WO 95/08536.

The current invention relates to a more efficient process of preparing compounds of formula I.

BRIEF SUMMARY OF THE INVENTION

The invention relates to a process of preparing a compound of formula I

I

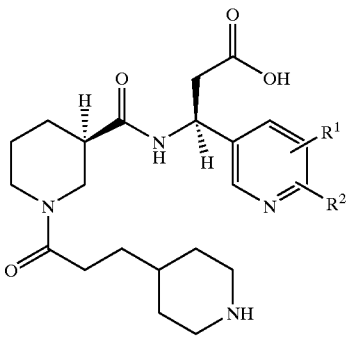

wherein $R^1$ and $R^2$ are independently selected from the group consisting of hydrogen, lower alkyl and halogen, comprising coupling 3-(N-benzyloxycarbonyl-4-piperidyl) propionic acid calcium salt of formula II as described herein, with (R)-(−)lower alkyl nipecotate-(+)-tartrate of formula III, as described herein to form a compound of formula IV

IV

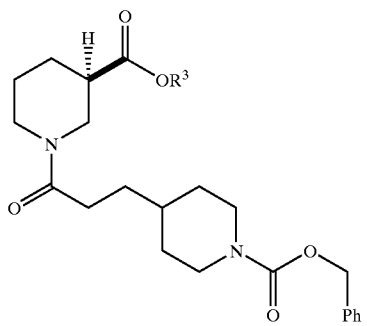

wherein $R^3$ is lower alkyl and Ph is phenyl, reacting the compound of formula IV to form the compound of formula V

V

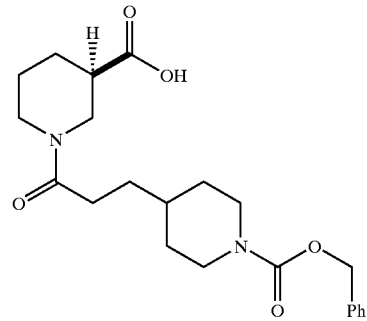

reacting the compound of formula V with a compound of formula VI

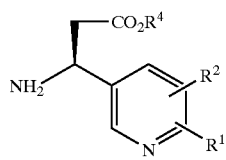

VI wherein R¹ and R² are as described above and R⁴ is lower alkyl or aralkyl, to form the compound of formula VII

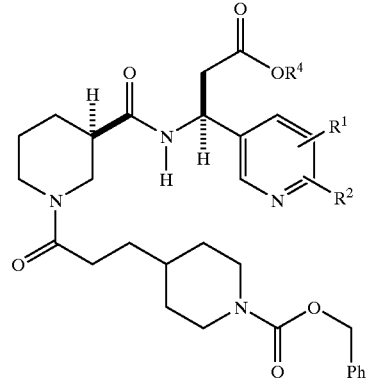

VII wherein R¹, R², R⁴, and Ph are as described above, reacting the compound of formula VII to form the compound of formula VIII

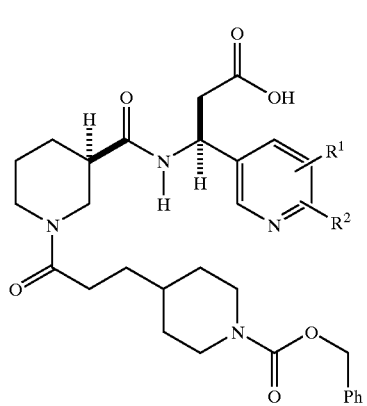

VIII wherein R¹, R² and Ph are as described above, reacting the compound of formula VIII to form the compound of formula I.

In another aspect, the claimed invention relates to a process of preparing the compound of formula VI, preferably methyl(S)-3-amino-3-(3-pyridyl) propanoate, an intermediate in the synthesis of a compound of formula I, by classical resolution of racemic methyl 3-amino-3-(3-pyridyl) propanoate using (+)-tartaric acid. This new process led to a more cost effective and volume efficient synthesis of enantiomerically pure methyl (S)-3-amino-3-(3-pyridyl) propanoate in good yield and high purity.

Another aspect of the claimed invention relates to a process for preparing the intermediate (R)-(−)lower alkyl nipecotate (+) tartrate salt which involves resolving racemic (±)lower alkyl nipecotate using (+) tartaric acid in an isopropyl alcohol and water mixture.

A further aspect of the claimed invention relates to the purification of the compound of formula I by dissolving the free base of formula I in an organic solvent and adjusting the pH in the range of from about 4 to about 12 in the presence of an organic amine base to precipitate the purified compound of formula I.

Costanzo, et al., in WO97/41102, Nov. 6, 1997 disclose the compound of formula Ia as a free base. A further aspect of the claimed invention relates to a novel crystalline form of the compound of formula Ia.

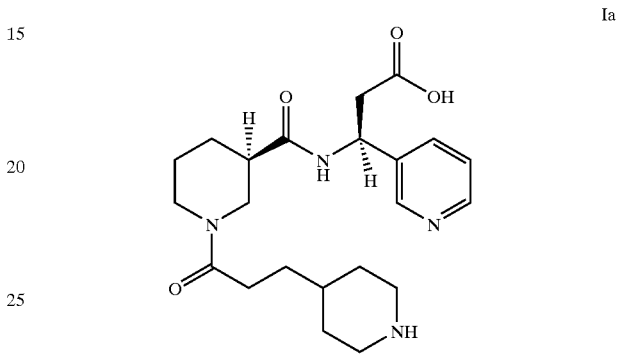

Ia

DETAILED DESCRIPTION OF THE INVENTION

As used herein, the term "alkyl" whether used alone or as part of a substituent group, include straight and branched chains. For example, alkyl radicals include methyl, ethyl, n-propyl, isopropyl, n-butyl, isobutyl, sec-butyl, t-butyl, n-pentyl and the like. Unless otherwise noted, "lower" when used with alkyl means a carbon chain composition of 1–4 carbon atoms.

As used herein, unless otherwise noted, "aralkyl" shall mean any lower alkyl group substituted with an aryl group such as phenyl, naphthyl and the like.

The term "halogen" means fluorine, chlorine, iodine or bromine.

With reference to substituents, the term "independently" means that when more than one of such substituents is possible, such substituents may be the same or different from each other.

The term "hydrogenation catalyst" shall mean a catalyst of rhodium (Rh), palladium (Pd) or platinum (Pt) which is adsorbed on a solid support such as Rh on carbon, Pd on carbon, Pd(OH)₂ on carbon or Pt on carbon or unsupported such as PtO₂.

In a preferred embodiment of the invention, the process relates to a process of preparing a compound of formula I wherein R¹ and R² are hydrogen.

The invention relates to a process of preparing a compound of formula I as more fully described in the schemes below.

SCHEME 1
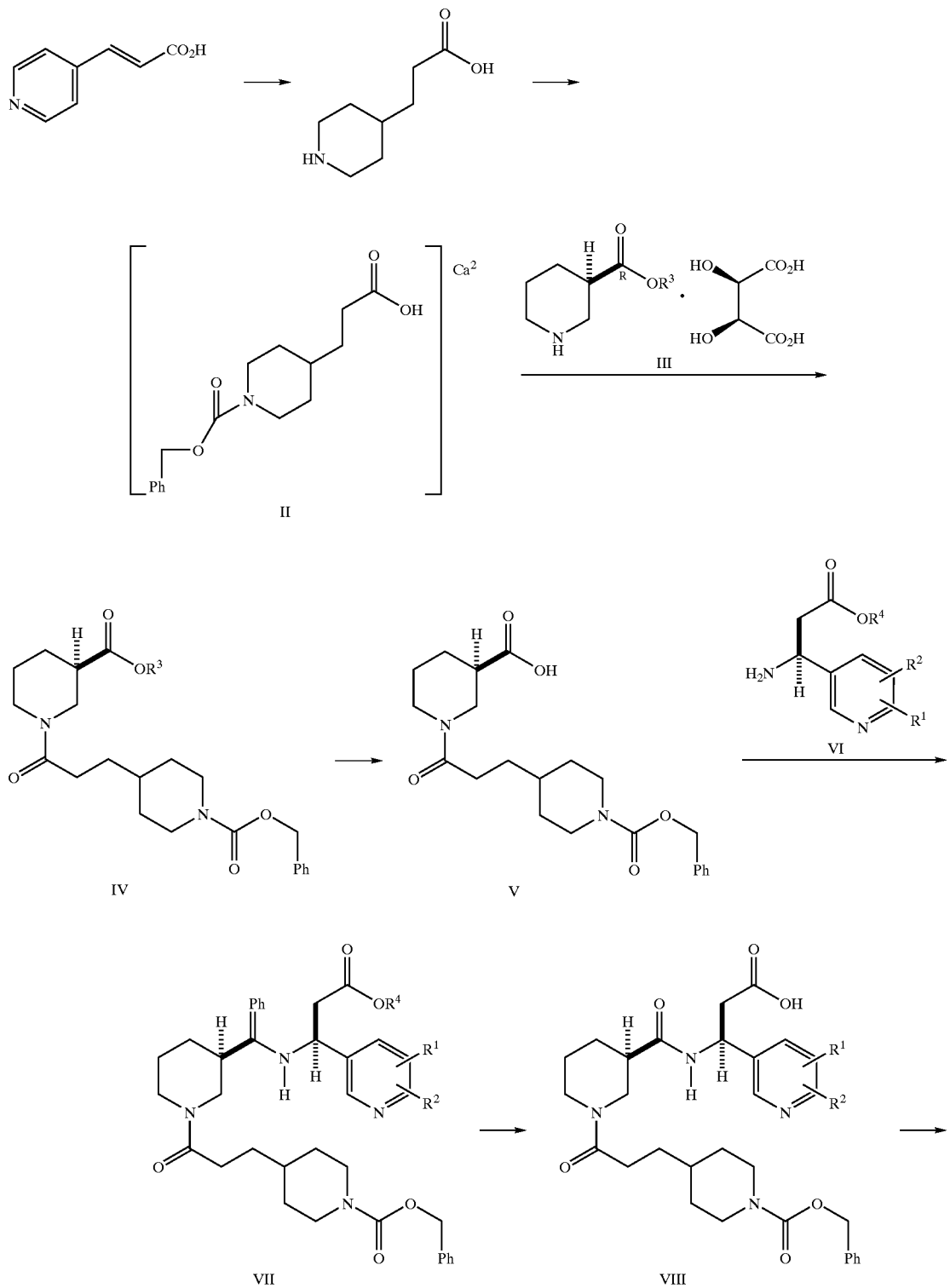

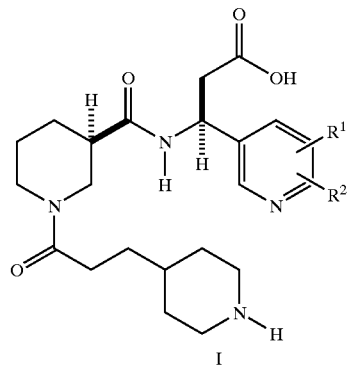

As set forth in Scheme 1 above, 3-(4-pyridine)acrylic acid, a known compound, is reduced to 3-(4-piperidyl) propionic acid by catalytic hydrogenation in a basic solvent such as inorganic bases, for example, alcoholates, hydroxide, hydrogen carbonate, carbonate of alkali or earth alkali metals or ammonia; or organic bases, for example, primary, secondary, or tertiary alkylamines, in aqueous or alcoholic solution, preferably aqueous ammonia, in the presence of a rhodium catalyst, preferably rhodium on $Al_2O_3$ at a temperature of from about room temperature to about 95°, preferably 80–95° C. at a pH in the range of about 7–13, preferably about 7–8.

3-(4-Piperidyl)propionic acid is reacted with a reagent capable of placing a benzyloxy carbonyl protecting group on an amine such as N-(benzyloxy carbonyloxy) succinimide ($Cb_2OSu$), N-benzyloxy carbonyloxy-5-norbornene-2,3-dicarboximide, or benzyl chloroformate, preferably benzyl chloroformate in a basic calcium salt, such as aqueous $Ca(OH)_2$ or calcium carbonate, preferably $Ca(OH)_2$, at a temperature in the range of from 0 to room temperature, preferably 0–10° C. and preferably at a pH in the range of about 8–14, preferably about 11–14, to form the 3-(N-benzyloxycarbonyl-4-piperidyl) propionic acid calcium salt of formula II.

The salt of formula II is reacted with (R)-(-)lower alkyl nipecotate tartrate of formula III, a known compound or compound prepared by known methods (J. Org. Chem., 1974, 39(7), 893; Eur., J. Pharmacol., 1983, 89(3–4)217), in the presence of a coupling reagent such as 1,3-dicylcohexyl carbodiimide (DCC), O-benzotriazole-1-yl-N,N,N',N'-tetramethyluronium hexafluorophosphate (HBTU), or 1-(3-dimethylaminopropyl)-3-ethylcarbodiimide hydrochloride, preferably DCC, in the presence of 0 to 1 equivalents, preferably 0.1 equivalents, of an additive such as 1-hydroxybenzotriazole hydrate (HOBT) or 3,4-dihydro-3-hydroxy-4-oxo-1,2,3-benzotriazine (HOOBT), preferably HOBT, in a solvent mixture of an organic solvent and water, such as, ethyl acetate/water or tetrahydrofuran/water or a polar organic solvent, such as dimethylformamide or 1-methyl-2-pyrrolidinone (NMP), at a 30 temperature in the range of from 0–50° C. preferably 15–25° C. and at a pH in the range of from about 6–10, preferably about 6–7, to form the corresponding compound of formula IV.

The compound of formula IV is hydrolyzed in an inorganic base such as lithium hydroxide, sodium hydroxide, preferably lithium hydroxide, in an organic solvent such as THF or dioxane, at a temperature in the range of from about 0 to about 50° C., preferably 5–25° C. at a pH preferably in the range of about 10 to about 13, to form the compound of formula V.

The compound of formula V is reacted with a carboxylic acid salt of the compound of formula VI, preferably the tartrate salt, in the presence of a coupling reagent such as 1,3-dicyclohexylcarbodiimide (DCC), 0-benzotriazole-1-yl-N,N,N',N'-tetramethyluronium hexafluorophosphate (HBTU), or 1-(3-dimethylaminopropyl)-3-ethylcarbodiimide hydrochloride, preferably DCC, in the presence of 0 to 1 equivalents, preferably 0.1 equivalents of an additive such as 1-hydroxybenzotriazole hydrate (HOBT) or 3,4-dihydro-3-hydroxy-4-oxo-1,2,3-benzotriazine (HOOBT), preferably HOBT, preferably DCC and HOBT, in the presence of a calcium salt such as calcium hydroxide, calcium carbonate, and the like, preferably calcium hydroxide, in an amount of at least 1 equivalent, to form the corresponding compound of formula VII, in a solvent mixture of an organic solvent and water, such as, ethyl acetate/water or tetrahydrofuran/water or a polar organic solvent, such as dimethylformamide or 1-methyl-2-pyrrolidinone (NMP) at a temperature in the range of from 0–50° C. preferably 15–25° C. and at a pH in the range of from about 6–10, preferably about 6–7.

Alternatively, the compound of formula V is reacted with a compound of formula VI or an inorganic salt thereof, preferably HCl salt, a known compound or compound prepared by known methods WO 97/41102, in the presence of a coupling reagent such as 1,3-dicyclohexylcarbodiimide (DCC), 0-benzotriazole-1-yl-N,N,N',N'-tetramethyluronium hexafluorophosphate (HBTU), or 1-(3-dimethylaminopropyl)-3-ethylcarbodiimide hydrochloride, preferably DCC, in the presence of 0 to 1 equivalents, preferably 0.1 equivalents of an additive such as 1- hydroxybenzotriazole hydrate (HOBT) or 3,4-dihydro-3-hydroxy-4-oxo-1,2,3-benzotriazine (HOOBT), preferably HOBT, preferably DCC and HOBT, to form the corresponding compound of formula VII, in a polar organic solvent such as acetonitrile, DMF, NMP, preferably acetonitrile, in the presence of an organic base such as triethylamine, diisopropylethylamine (DIPEA) or 4-methyl morpholine (NMM), preferably NMM, at a temperature in the range of 0–35° C., and at a pH in the range of about 7–11, preferably in the range of about 8–10.

The compound of formula VII is reacted in an organic solvent, such as THF, dioxane, or DMF, preferably THF, in the presence of an inorganic base such as sodium hydroxide, or lithium hydroxide, preferably lithium hydroxide, at a temperature in the range of from 0–40° C., preferably 10–15° C., preferably at a pH in the range of about 8–11. The resulting mixture is acidified with an inorganic acid such as sulfuric, hydrochloric, and the like, preferably to a pH of about 3–5, to yield the corresponding compound of formula VIII. When the mixture is acidified with sulfuric acid, the acidification results in the precipitation of N,N'-bis(2,2,2-trichloro-1-hydroxyethyl)urea (DCU), which is preferably removed prior to the next step.

The compound of formula VIII is converted to the corresponding compound of formula I via catalytic hydrogenation using a hydrogenation catalyst, preferably a palladium catalyst such as Pd/C, in a polar solvent such as an alcohol, preferably methanol or ethanol, at a temperature of from 30–50° C.

The compound of formula I is purified by heating the compound of formula I in an organic solvent such as ethylacetate, methyl t-butyl ether, methanol, ethanol, n-butanol and the like, preferably n-butanol, to a temperature up to 85° C., preferably 75–85° C. The solution is then cooled to a temperature in the range of about 20–30° C. An amine organic base such as triethylamine, cyclohexylamine, t-butylamine and the like, preferably t-butylamine, is added in an amount sufficient to result in a pH in the range of about 4–12, preferably about 7–11, most preferably 7.5.

isopropanol, toluene and mixtures thereof, with at least one equivalent of gaseous NH3 at a temperature in the range of from 40–100° C., preferably 60–65° C. in the presence of a carboxylic acid such as acetic acid or formic acid.

The compound of formula X is reduced to the corresponding compound of formula XI, preferably by reacting with borohydride reagents such as sodium borohydride, in an organic solvent such as THF, in the presence of an organic acid such as propionic acid, benzoic acid, acetic acid, or trifluoroacetic acid (TFA), preferably acetic acid or TFA, at a temperature in the range of −5 to 10° C. at a pH in the range of about 1–6.

In the case where the compound of formula X is reduced by reacting with a borohydride reagent, the reaction is quenched with an alcohol, preferably methanol and a strong acid such as hydrochloric or sulfuric, preferably hydrochloric, to afford a compound of formula XI as a salt. The amine is freed by reacting the salt of the compound of formula XI with a tertiary amine such as triethylamine, DIPEA, or NMM, preferably triethylamine, in an organic solvent such as acetonitrile, THF, or dioxane, preferably acetonitrile. The resulting tertiary amine salt is separated by conventional methods such as filtration or extraction, preferably filtration, to afford the compound of formula XI as the free amino ester.

The compound of formula XI is heated in the presence of (+)-tartaric acid, preferably 0.25 equivalents of (+) tartaric acid, to a temperature resulting in the formation of a solution in a polar solvent, such as alcohol, for example, methanol or ethanol or an alcohol water mixture, such as methyl alcohol/water or ethyl alcohol/water, preferably ethyl alcohol/water mixture at a ratio of 90:10 to 100% ethanol, preferably at a ratio of 97:3 and cooled to a temperature in the range of 25–30° C. to form the corresponding salt of formula XII.

The tartrate salt of formula XII is converted to the corresponding compound of formula VI or salt thereof, by known methods. Preferably, the salt of formula XII is reacted with at least two equivalents, preferably between 8 and 11 equivalents, of gaseous HCl, in a polar solvent, such as methanol, ethanol, isopropyl alcohol, ethyl acetate or mixture thereof, at a temperature in the range of 0–50° C., preferably at about 10° C., to form the corresponding dihydrochloride salt of formula VI. When R⁴ is methyl, the preferred solvent is methanol.

SCHEME 2

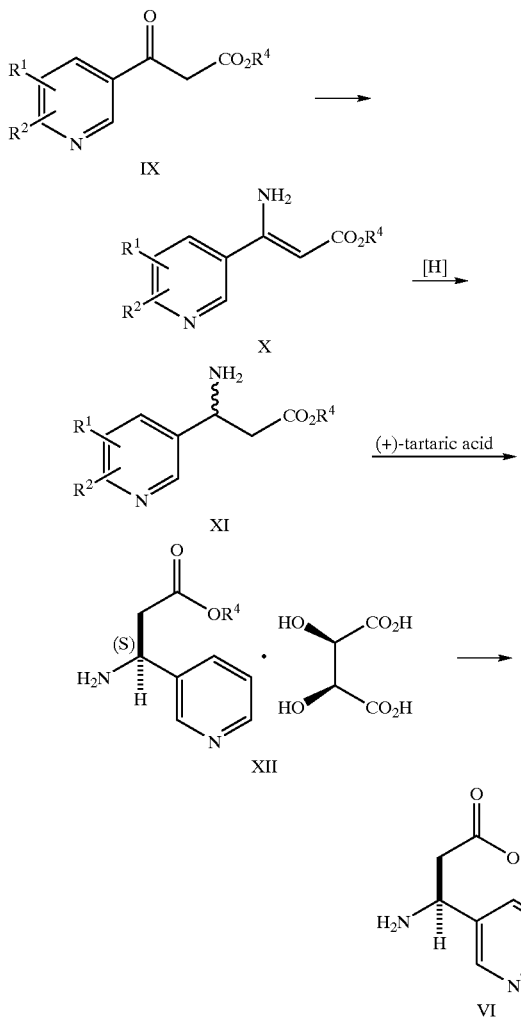

SCHEME 3

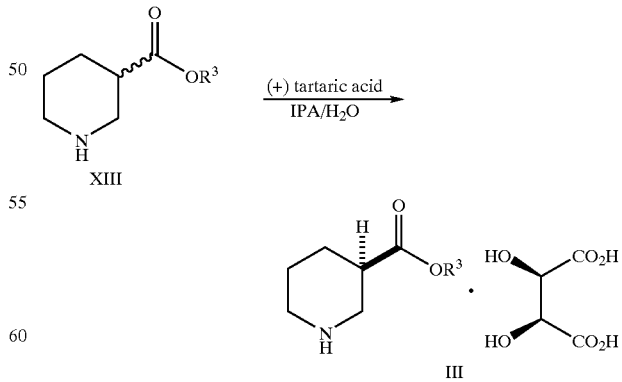

As set forth in Scheme 2 above, a compound of formula IX, a known compound or compound prepared by known methods, J. Am. Chem Soc 1957, Vol. 79, p. 159, is converted to a corresponding compound of formula X by dissolution in an organic solvent such as, methanol, As set forth in Scheme 3 above, the compound of formula XIII, a known compound or compound prepared by known methods (Eur. J. Pharmacol., 1983, 89(3–4),217), is reacted with (+)tartaric acid, preferably one equivalent (+) tartaric acid in a mixture of isopropyl alcohol (IPA) and water, preferably at a ratio of 90:10 up to 100% IPA, more preferably at a ratio of 94:6, and heating to form a solution, preferably at a temperature in the range of from 73–77° C. then cooled to no less than 20° C., preferably 26–30° C., to form the corresponding salt of formula III.

A further aspect of the present invention is a novel crystalline forms of the compound of formula Ia, characterized by its x-ray powder diffraction pattern, utilizing a Philips PW3710 based powder diffractometer using $CuK_\alpha$ radiation and the following system conditions:

CuKα radiation, 30 mA, 50KV b) Optics
   1/12° divergence slit
   0.2 receiving slit c) Scan 5.01 to 34.97° 2 θ at a scan rate of 0.020°/1.25 sec 2θ/second d) Aluminum sample holder The novel crystal form of the compound of formula Ia appears as irregular acicular particles crystals and may be characterized essentially by its X-ray diffraction pattern:

| POWDER X-RAY DIFFRACTION RESULTS | | |
|---|---|---|
| Angle °2θ | d Spacing (Å) | Relative Intensity (%) |
| 8.77 | 10.09 | 17.50 |
| 10.52 | 8.41 | 16.20 |
| 15.57 | 5.69 | 100.00 |
| 15.90 | 5.65 | 22.70 |
| 16.52 | 5.37 | 48.30 |
| 17.48 | 5.08 | 25.80 |
| 17.72 | 5.01 | 24.70 |
| 18.32 | 4.85 | 58.10 |
| 19.62 | 4.53 | 21.50 |
| 19.98 | 4.45 | 47.30 |
| 20.28 | 4.38 | 41.50 |
| 21.08 | 4.22 | 67.80 |
| 21.36 | 4.16 | 18.10 |
| 22.82 | 3.90 | 23.50 |
| 23.26 | 3.83 | 50.40 |
| 24.01 | 3.71 | 57.60 |
| 24.73 | 3.60 | 24.10 |
| 25.62 | 3.48 | 9.90 |
| 25.99 | 3.43 | 8.00 |
| 26.37 | 3.38 | 4.60 |
| 27.37 | 3.26 | 13.50 |
| 27.98 | 3.19 | 23.20 |
| 28.62 | 3.12 | 15.70 |
| 30.20 | 2.96 | 19.00 |
| 30.71 | 3.41 | 17.30 |
| 31.29 | 2.86 | 32.40 |
| 31.40 | 2.85 | 33.30 |
| 31.73 | 2.82 | 25.10 |
| 32.71 | 2.74 | 12.40 |
| 33.84 | 2.65 | 9.70 |
| 34.55 | 2.60 | 10.20 |

The following examples describe the invention in greater detail and are intended to illustrate the invention, but not to limit it.

EXAMPLE 1

3-(4-Piperidyl)propionic Acid 3-(4-pyridine)acrylic acid (18 kg) was added to 75 kg of water. The resulting suspension was stirred and neutralized (pH 7.5) with 6.8 kg of aqueous ammonia (25%). A slurry of $Rh/Al_2O_3$ (0.9 kg) in 5 kg of water was added to the reaction mixture, which was then made inert under nitrogen. The mixture was hydrogenated under a pressure of 3–3.5 bar at 85–95° C. After eight hours, when no further change in pressure was observed, the mixture was cooled to 25–35° C. The catalyst was filtered and washed with 4.0 kg of water. Ammonia and most of the water in the reaction mixture were removed under vacuum at 80–90° C., and the product began to precipitate. Acetonitrile (116 kg) was added and then the mixture was concentrated (ca. 50%) under vacuum. Additional acetonitrile (57.1 kg) was added to aid in crystallization and the reaction mixture was stirred for 1–4 hours at 15–25° C. until precipitation of the product was complete. The product was centrifuged and oven dried under vacuum at 45–55° C. to afford 19.1 kg (100%) of the title compound.

EXAMPLE 2

Di 3-(N-Benzyloxycarbonyl-4-piperidyl)propionic Acid Calcium Salt 3-(4-Piperidyl)propionic acid (20.0 g, 0.12 mol) and calcium hydroxide (14.1 g, 0.19 mol) were suspended in 47 g water and 195 g acetonitrile at 15–25° C. and then cooled to 0–10° C. Benzyl chloroformate (23.9 g, 0.14 mol) was added within 30 minutes and the reaction stirred at 0–5° C. for 2 h. The product precipitated during the reaction and was isolated by filtration to afford the title compound in 95% yield.

EXAMPLE 3

(R)-(−)-Ethyl Nipecotate Tartrate

L-(+)-Tartaric acid (47.74 g, 318 mmol) was suspended in 265 g of isopropyl alcohol and 16.91 g of water. The mixture was heated to 60–65° C. to afford a homogeneous solution. One equivalent of (±)-ethyl nipecotate (50 g, 318 mmol) was added while the temperature was maintained at or below 75° C. The mixture was stirred at 70–75° C. for 20–30 minutes, then cooled to 60° C. over 60 minutes. Seed crystals of (R)-(−)-ethyl nipecotate-L-(+)-tartrate (25 mg, 0.08 mmol) were added and the reaction was cooled to 26–30° C. over three hours. The temperature was maintained at 26–30° C. for 30 minutes until precipitation was complete. The product was isolated (62.0 g, 94.8% de) and washed twice with a mixture of isopropyl alcohol (21.05 g) and water (1.34 g). The crude product was slurried in a mixture of isopropyl alcohol (188 g) and water (12 g) at 73–77° C. After stirring for 10–20 minutes, the suspension was cooled to 26–30° C. Temperatures exceeding 30° C. will result in less yield, while a temperature of less than 25° C. resulted in de<98%. The product was isolated by filtration and washed twice with a mixture of isopropyl alcohol (21.05 g) and water (1.34 g). This afforded the title compound as a white powder in 72% yield, 98.8% de.

EXAMPLE 4

(R)-1-[3-(1-Benzyloxycarbonyl-4-piperidyl)-propionyl]-3-piperidinecarboxylic Acid 3-(N-Benzyloxycarbonyl-4-piperidyl)propionic acid calcium salt (21.9 g, 32.2 mmol), (R)-ethyl nipecotate (21.7 g, 70.8 mmol), and hydroxy benzyltriazole (HOBT) (1.30 g, 9.65 mmol) were suspended in water (40 g) and THF (80 g). The resulting suspension was adjusted to pH 7 with $Ca(OH)_2$. Ca-tartrate precipitated and was collected by filtration and washed with 10 g THF. To the filtrate was added slowly a solution of DCC (19.9 g, 96.5 mmol) in 40 g of THF at 0–5° C. The reaction mixture was warmed slowly to 20–25° C. and N,N-dichlorourethane (DCU) precipitated. After 4 h, the DCU was removed by filtration and washed with 8 g of THF. The filtrate was cooled to 0–5° C. and lithium hydroxide (6.67 g, 159.0 mmol) in 60.38 g of water was added at 0–5° C. The pale yellow solution was warmed to ambient temperature. After 3 h, the solvent was removed by distillation under vacuum at or below 55° C. Ethyl acetate (45.4 g) was added and the pH was adjusted to exactly 4.0 with ca. 18.6 g of concentrated HCl. DCU precipitated and was filtered from the mixture. The layers were separated and the aqueous layer was washed twice with 31.8 g of ethyl acetate. The combined organic layers were washed twice with a solution of 15.8 g NaCl in 47.2 g of water. The ethyl acetate layer was separated and the solvent was removed by distillation under vacuum at or below 55° C. The product remained as a thick pulp. MTBE (70.8 g) was added and the suspension was stirred for 30 minutes at 45–50° C., then cooled to 15–25° C. and stirred for one hour until crystallization was complete. The product was centrifuged and washed with 6.3 g of MTBE, then dried under vacuum at 40–50° C. to afford the title compound in 92% yield and >98% ee.

EXAMPLE 5

Methyl (S)-3-Amino-3-(3-pyridyl)propanoate Dihydrochloride

Two separate procedures were developed to synthesize this compound. The first procedure (A) involved two steps for the production of enantiomerically pure methyl(s)-3-amino-3-(3-pyridyl)propanoate dihydrochloride via NaBH$_4$ reduction. The second procedure (B) involved three steps for the production of enantiomerically pure methyl(S)-3-amino-3-(3-pyridyl)propanoate dihydrochloride via hydrogenation.
Procedure A:
Methyl 3-Amino-3-(3-pyridyl)-2-propenoate A suspension of methyl nicotinoylacetate dihydrochloride (50.0 g, 0.23 mol, dried) and sodium acetate (19.0 g, 0.23 mol) in glacial acetic acid (1.4 g, 0.02 mol), toluene (50 g), and methanol (50 g) was heated to 60–65° C. Ammonia (14.0 g, 0.82 mol) was bubbled through the suspension. After four hours, no starting material was present by HPLC. Two-thirds of the solvents were removed by distillation. The solution was stirred at 0° C. for one hour, and the precipitate was collected by filtration and dried to yield 83% of methyl 3-amino-3-(3-pyridyl)-2-propenoate. The crude product was used as is without further purification.
Methyl 3-Amino-3-(3-pyridyl)propanoate Dihydrochloride Glacial acetic acid (526.9 g, 8.78 mol) was added dropwise at <–5° C. to a suspension of methyl 3-amino-3-(3-pyridyl)-2-propenoate (0.45 mol) and sodium borohydride (44.3 g, 1.17 mol) in THF (500 g) and the resulting reaction mixture was stirred at –5–0° C. After 5 h, methanol (600 g) was added dropwise to the solution at –5–0° C. After 0.5 hours, HCl (163 g, 4.47 mol) was bubbled through the solution and stirred at 0° C. After 8 h, the white precipitate was filtered off and dried at 40° C. to yield 101.6 g (89%) of methyl 3-Amino-3-(3-pyridyl)propanoate dihydrochloride.
Procedure B:
Methyl 3-Amino-3-(3-pyridyl)-2-propenoate Methyl nicotinoylacetate (88 g, 0.5 mol) was dissolved in toluene (200 g), isopropyl alcohol (200 g), and formic acid (98–100%, 1.22 g, 0.03 mol) and heated to 60–65° C. Gaseous ammonia (23 g, 1.35 mol) was bubbled through the solution for 15 minutes. The white suspension was stirred at 65° C. until a homogeneous solution formed. The solution was stirred for two hours at 65° C. and then concentrated (ca. 200 g) at 65° C. The residue was cooled to –5° C. with stirring and methyl 3-amino-3-(3-pyridyl)-2-propenoate crystallized as colorless needles. The process of reducing the volume to 50% followed by cooling was repeated three times with the mother liquors. Filtration, washing with toluene, and drying at 30° C. resulted in 77.74 g (88.8%) of methyl 3-amino-3-(3-pyridyl)-2-propenoate as colorless crystals.
Methyl 3-Amino-3-(3-pyridyl)propanoate Dihydrochloride Dry palladium on charcoal (0.54 g, manufactured by Degussa, 5% Pd/C) was added to a solution of methyl 3-Amino-3-(3-pyridyl)-2-propenoate (5.4 g, 30 mmol) in dry acetic acid (13 g) in a 450 ml Pyrex high-pressure bottle. The reaction mixture was hydrogenated at 3–3.2 bar. After 1.5–2 h, the catalyst was filtered and washed with 20 g of isopropyl alcohol until the wash solvent was no longer yellow. Gaseous HCl (10.6 g, 0.3 mol) was bubbled through the stirred filtrate at 5–15° C. The suspension was cooled to 0–5° C. and stirred for two hours. The resulting white precipitate was filtered, washed with 5 g of isopropyl alcohol, and dried at 45° C. to yield 5.95 g (78.4%,) of methyl 3-Amino-3-(3-pyridyl)propanoate dihydrochloride.

EXAMPLE 6

Methyl (S)- 3-Amino-3-(3-pyridyl)propanoate Dihydrochloride

Racemic methyl 3-amino-3-(3-pyridyl)propanoate dihydrochloride(150 g, 0.563 mol) was suspended in acetonitrile (425 g). Triethylamine (125.3 g, 1.239 mol) was added dropwise while the temperature was maintained at 35° C. or less. The reaction was stirred for a minimum of two hours at 20° C. then cooled to 5° C. After 0.5 hours the resulting precipitate was centrifuged and washed with 50 g of acetonitrile. The acetonitrile was removed by distillation at 40–45° C. to afford crude free base of methyl 3-amino-3-(3-pyridyl)propanoate dihydrochloride. The free base (ca. 105 g) was dissolved in 80 g of ethanol. A solution of (+)-tartaric acid (21.1 g, 0.141 mol) in 80 g of ethanol and 5 g of water was added. The reaction mixture was stirred for 4 hours at 20–23° C. The suspension was cooled slowly to 10–15° C., then stirred for an additional two hours. The precipitate was filtered off and washed with 30 g of ethanol.

The crude tartrate salt was slurried at 35–40° C. for two hours in a mixture of 150 g of ethanol and 4.6 g of water. The mixture was stirred for 0.5 hours at 25° C. The resulting precipitate was isolated and washed with 30 g of ethanol. Up to three slurries may be necessary to achieve a >98% de. The precipitate was suspended in methanol (100 g) and a minimum of 10 equiv. HCl gas (51.3 g, 1.408 mol) was added. The reaction mixture was stirred at 22–28° C. until the reaction was complete by HPLC. Ethyl acetate (160 g) was added and the reaction mixture was stirred at 0–5° C. for three hours. The precipitate was filtered and washed with 30 g of cold (0–5° C.) methanol. The product was dried under vacuum at 35–45° C. to yield 39.46 g of the title compound as a white solid (28%, 55% of the desired S-enantiomer).

EXAMPLE 7

[S-(R*,S*)]-β-[[[1-[1-Oxo-3-(4-piperidinyl)propyl]-3-piperidinyl]carbonyl]amino]-3-pyridine Propanoic Acid (R)-1-[3-(1-benzyloxycarbonyl-4-piperidyl)-propionyl]-3-piperidinecarboxylic acid (60 kg, 149 mol) and HOBT (1.98 kg, 14.8 mol) were suspended in acetonitrile (164 kg) at 0–5° C. NMM (33.2 kg, 328.5 mol) and methyl (S)-3-amino-3-(3-pyridyl)propanoate dihydrochloride (39.2 kg, 154.9 mol) were added to the reaction mixture. After 1 h, a solution of DCC (37.2 kg, 180.3 mol) in acetonitrile (117 kg) was added at 0–5° C. The mixture was warmed to 20–25° C. and stirred for 12 hours. The suspension was cooled to 0–5° C. and the precipitated DCU was filtered off and washed with 81 kg of pre-cooled ethyl acetate. The solvent was distilled from the filtrate, and the residual oil was dissolved twice in 50 kg of ethyl acetate and the solvent removed. The resulting oil was dissolved in 162 kg of ethyl acetate and washed three times with a solution of 6.3 kg of NaHCO$_3$ in 120 kg of water to remove excess HOBT. The solvent was removed from the organic layer and the resulting oil and/or foam was dissolved twice in 50 kg of THF and evaporated to dryness to afford methyl [S-(R*,S*)-β-[[[1-[1-oxo-3-(1-benzyloxycarbonyl-4-piperidinyl)propyl]-3-piperidinyl] carbonyl]amino]-3-pyridine propanoate as an oil.

Crude methyl [S-(R*,S*)-β-[[[1-[1-oxo-3-(1-benzyloxycarbonyl-4-piperidinyl)propyl]-3-piperidinyl] carbonyl]amino]-3- pyridine propanoate was dissolved in 163 kg of THF at 45° C. The clear solution was cooled to 0–5° C. and within 30 to 60 minutes a solution of lithium hydroxide monohydrate (14.3 kg, 340.8 mol) in 151 kg of water was added to the reaction mixture. The pale yellow solution was stirred for 2 h at 20–25° C. HCl (36–38%, 38 kg) was added to achieve a pH of 4.1. NaCl (7.2 kg) was added and the layers were separated. The organic layer was washed twice with a solution of 36.4 kg of NaCl in 72.6 kg of water. The organic layers were distilled and the resulting oil was dissolved in 75 kg of THF. The solvent was removed until a water content of <2% was achieved. The precipitated inorganic salts were removed and washed with 9 kg of THF. The filtrate was evaporated under vacuum at 45° C. to afford [S-(R*,S*)-β-[[[1-[1-oxo-3-(1-benzyloxycarbonyl-4-piperidinyl)propyl]-3-piperidinyl]carbonyl]amino]-3- pyridine propanoic acid as an oil.

Crude [S-(R*,S*)-β-[[[1-[1-oxo-3-(1-benzyloxycarbonyl-4-piperidinyl)propyl]-3-piperidinyl] carbonyl]amino]-3- pyridine propanoic acid was dissolved in 312 kg of methanol. A suspension of 60 kg of methanol and 15 kg of slurried Pd/C (wet) was added to the reaction mixture, which was then hydrogenated under pressure (2–3 bar) with stirring at 38–42° C. When the hydrogenation was finished, the catalyst was filtered through Hyflo SuperCel and washed with 39 kg of methanol. The filtrate was reduced to a colorless oil under reduced pressure at 40–50° C. The crude product was dissolved in 60 kg of n-butyl alcohol and concentrated to an oil, which began to bubble or foam. The crude product was slurried in 756 kg of n-butyl alcohol and heated to 75–85° C. for 15–20 minutes, then cooled to 20–30° C. t-Butylamine (0.7 kg) was added (pH 7.5) and the reaction was stirred. The reaction mixture was cooled to 0–5° C. and stirred for an additional hour. The precipitate was isolated, washed with 102 kg of MTBE, and dried under vacuum at 60–80° C. to yield 36 kg (58%) of the title compound as a white crystalline solid.

Example 8

[S-(R*,S*)]-β- [[[1-[1-Oxo-3-(4-piperidinyl)propyl]-3-piperidinyl]carbonyl]amino]-3-pyridine Propanoic Acid (R)-1-[3-(1-benzyloxycarbonyl-4-piperidyl)-propionyl]-3-piperidinecarboxylic acid (1 kg, 2.48 mol), methyl (S)-3-amino-3-(3-pyridyl)propanoate tartrate (where the tartrate is present as a hemi-tartrate) (0.7 kg, 2.73 mol) and HOBT (38 g, 0.25 mol) were added to a reaction vessel. To the mixture was added a previously prepared cold solution (0–5° C.) of KH$_2$PO$_4$ (96.8 g, 0.71 mol) and Na$_2$HPO$_4$ (69.2 g, 0.49 mol) in water (3 kg) and THF (2 kg). The pH was then adjusted to 6.0–6.4 using calcium hydroxide (110 g). The resulting suspension was cooled to 0–5° C. and a solution of DCC (564 g, 2.73 mol) in THF (1 kg) was added. The mixture was stirred for 1 h at 0–5° C., warmed to 20–25° C. and stirred for 4 h. The suspension was cooled to 0–5° C. and ethyl acetate (2 kg) was added. After 15 minutes, the precipitate (a mixture of DCU and calcium tartrate) was filtered off and washed with pre-cooled THF (1 kg). The phases were separated and the organic phase was washed with 5% NaHCO$_3$ (1 kg). The organic phase was concentrated at 40–50° C., the residual oil was dissolved in THF (1 kg) and evaporated to dryness to afford methyl [S-(R*,S*)-β-[[[1-[1-oxo-3-(1-benzyloxycarbonyl-4-piperidinyl)propyl]-3-piperidinyl]carbonyl]amino]-3-pyridine propanoate as an oil.

Crude methyl [S-(R*,S*)-β-[[[1-[1-oxo-3-(1-benzyloxycarbonyl-4-piperidinyl)propyl]-3-piperidinyl] carbonyl]amino]-3- pyridine propanoate was dissolved in THF (1.4 kg) at 45° C. The clear solution was cooled to 0–5° C. Within 30–90 min, a solution of lithium hydroxide monohydrate (182 g, 4.21 mol) in water (1.9 kg), cooled to 5° C., was added to the reaction mixture. The solution was stirred for 0.5 h at 0–5° C., warmed to 20–25° C. and stirred for an additional 1 h. The reaction mixture was cooled to 0–5° C. and treated with a solution of sulfuric acid (250 g) in water (1.14 kg) to achieve a pH of 3.9–4.1. The precipitated DCU was collected by filtration and washed with THF (400 g). The resulting phases were separated and the organic phase washed with a saturated NaCl solution (1 kg). The organic layer was distilled and the resulting oil dissolved in THF (2 kg). The solvent was removed until a water content of <2% was achieved. The precipitated inorganic salts were removed. The filtrate was concentrated and the resulting oil dissolved in MeOH (2 kg). The solution was evaporated under vacuum at 45° C. to afford [S-(R*,S*)-β-[[[1-oxo-3-(1-benzyloxycarbonyl-4-piperidinyl)propyl]-3-piperidinyl] carbonyl]amino]-3-pyridine propanoic acid as an oil.

Crude [S-(R*,S*)-β-[[[1-[1-oxo-3-(1-benzyloxycarbonyl-4-piperidinyl)propyl]-3-piperidinyl] carbonyl]amino]-3- pyridine propanoic acid was dissolved in a suspension of Pd/C (261 g) in MeOH (3 kg). The reaction mixture was hydrogenated under pressure (2–3 bar) with stirring at 30–40° C. After 6 h, the catalyst was filtered through Hyflo SuperCel and washed with methanol (1.04 kg). The filtrate was concentrated under reduced pressure at 40–50° C. The crude product was dissolved in n-butyl alcohol (1 kg) and concentrated to an oil. The crude product was taken up in n-butyl alcohol (1.7 kg) and heated to 75–85° C. for 1–3 h, then cooled to 20–30° C. for 2–3 h. The resulting suspension was cooled to 0–5° C. and stirred for an additional 1 h. The precipitate was isolated, washed with MTBE (1.7 kg), and dried under vacuum at 60–80° C. to yield 36 kg (53%) of the title compound as a white crystalline solid.

What is claimed is:
1. A process for preparing a compound of formula I

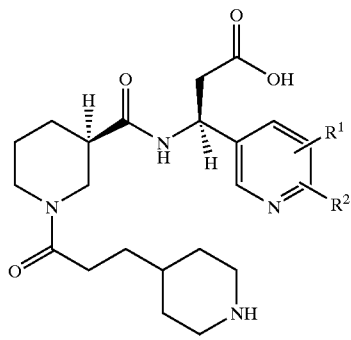

I wherein $R^1$ and $R^2$ are independently selected from the group consisting of hydrogen, lower alkyl and halogen, comprising reacting the salt of formula II

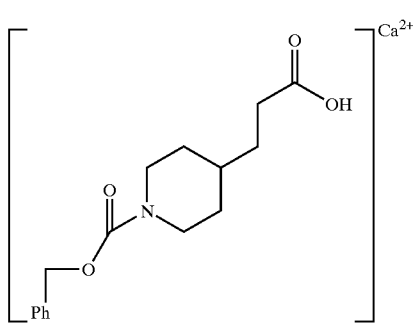

II with the salt of formula III

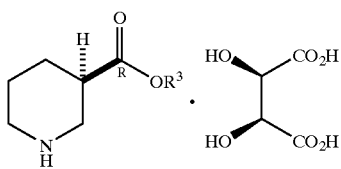

III wherein $R^3$ is lower alkyl
at a pH in the range of about 6 to 10
to form the compound of formula IV

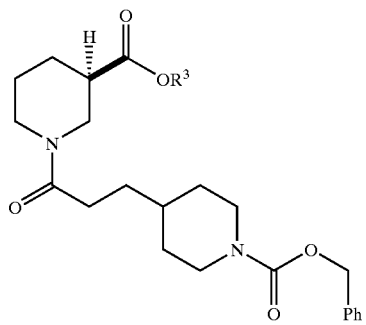

IV reacting the compound of formula IV to form the compound of formula V

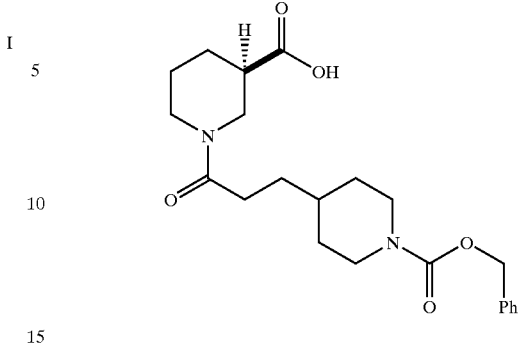

V reacting the compound of formula V with a compound of formula VI

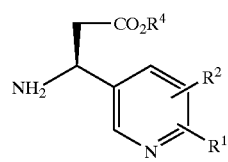

VI at a pH in the range of about 7 to 11
to form the compound of formula VII

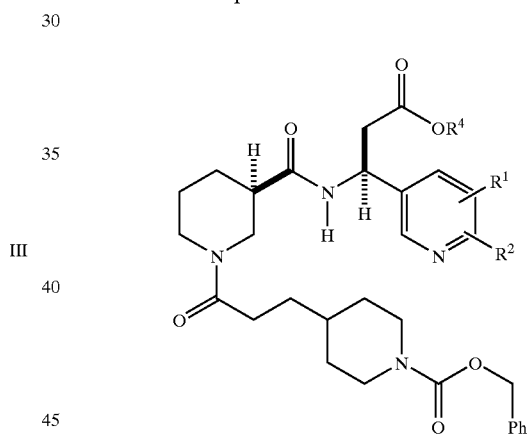

VII reacting the compound of formula VII to form the compound of formula VIII

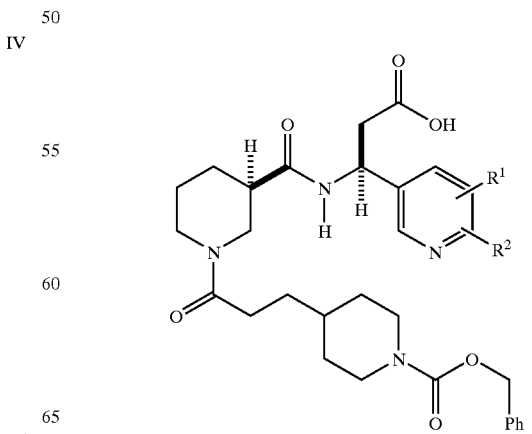

VIII and reacting the compound of formula VIII with hydrogen in the presence of a hydrogenation catalyst to form the compound of formula I.

2. The process of claim 1, wherein in the compound of formula I $R^1$ and $R^2$ are hydrogen.

3. A process for preparing a compound of formula VI

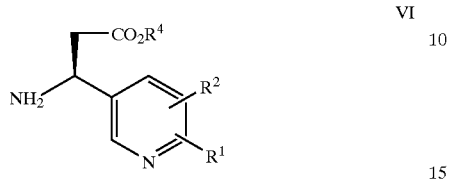

wherein $R^1$ and $R^2$ are independently selected from hydrogen, lower alkyl and halogen, and $R^4$ is lower alkyl or aralkyl, or salt thereof comprising reacting a compound of formula XI

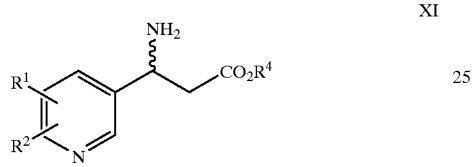

with (+)tartaric acid to form the salt of formula XII

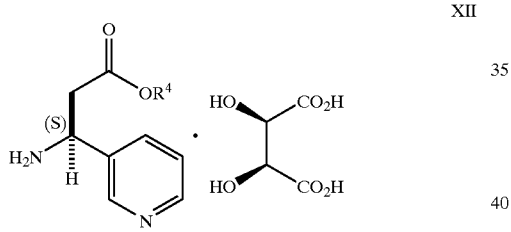

and reacting the salt of formula XII to form the compound of formula VI or salt thereof.

4. The process of claim 3, wherein in the compound of formula XI $R^4$ is methyl and the (+)tartaric acid is present in an amount of 0.25 equivalents.

5. The process of claim 4, wherein in the compound of formula VI, $R^1$ and $R^2$ are hydrogen and $R^4$ is methyl.

6. The process of claim 4, wherein the salt of formula XII is reacted with gaseous HCl in methanol to form the dihydrochloride salt of formula VI.

7. A process of preparing a salt of formula III

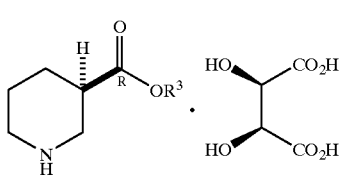

wherein $R^3$ is lower alkyl comprising reacting a compound of formula XIII

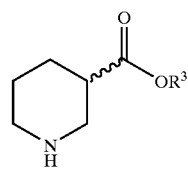

with (+)tartaric acid in a mixture of isopropyl alcohol and water.

8. The process of claim 7, wherein in the salt of formula III, $R^3$ is ethyl.

9. The process of claim 8, wherein in the mixture of isopropyl alcohol and water the isopropyl alcohol is present in a ratio of from 90 percent isopropyl alcohol to 10 percent water to 100 percent isopropyl alcohol.

10. A process of purifying a compound of formula I

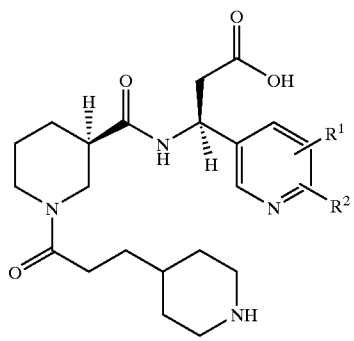

wherein $R^1$ and $R^2$ are independently selected from the group 25 consisting of hydrogen, lower alkyl and halogen, comprising reacting the free base of formula I at a pH in the range of from about 4 to 12 in the presence of an organic amine base.

11. The process of claim 10, wherein in the compound of formula I $R^1$ and $R^2$ are hydrogen.

12. The process of claim 11, wherein the organic amine base is triethylamine, cyclohexylamine, or t-butylamine and the reaction is carried out at a pH in the range of from about 7 to 11.

13. The process of claim 12, wherein the reaction is carried out at a pH of 7.5.

14. The process of claim 13, wherein the organic amine base is t-butylamine.

15. A process for preparing a compound of formula VIII

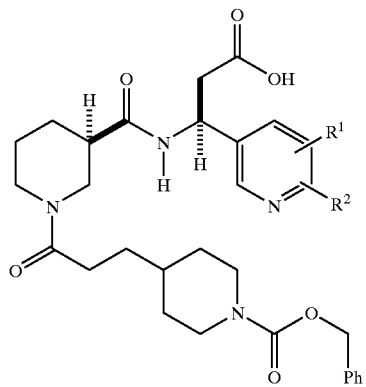

wherein $R^1$ and $R^2$ are independently selected from the group consisting of hydrogen, lower alkyl and halogen, comprising reacting a compound of formula V

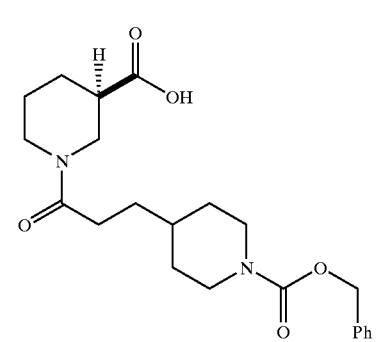

wherein Ph is phenyl, with a carboxylic acid salt of a compound of formula VI

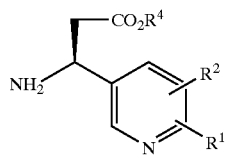

wherein $R^1$ and $R^2$ are independently selected from the group consisting of hydrogen, lower alkyl and halogen, and $R^4$ is lower alkyl or aralkyl,
in the presence of a calcium salt, in an amount equal to at least 1 equivalents, at a pH in the range of about 6–10.

16. The process of claim 15, wherein the carboxylic acid salt of the compound of formula VI is tartrate salt.

17. The process of claim 15, wherein the calcium salt is calcium hydroxide.

18. The process of claim 15, wherein the pH is in the range of about 6–7.

19. A crystalline form of the compound of formula Ia

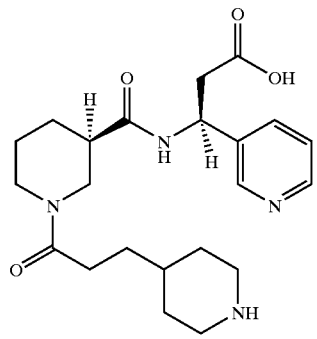

characterized essentially by the following X-ray diffraction pattern:

| Angle °2θ | d Spacing (Å) | Relative Intensity (%) |
|---|---|---|
| 8.77 | 10.09 | 17.50 |
| 10.52 | 8.41 | 16.20 |
| 15.57 | 5.69 | 100.00 |
| 15.90 | 5.65 | 22.70 |
| 16.52 | 5.37 | 48.30 |
| 17.48 | 5.08 | 25.80 |
| 17.72 | 5.01 | 24.70 |
| 18.32 | 4.85 | 58.10 |
| 19.62 | 4.53 | 21.50 |
| 19.98 | 4.45 | 47.30 |
| 20.28 | 4.38 | 41.50 |
| 21.08 | 4.22 | 67.80 |
| 21.36 | 4.16 | 18.10 |
| 22.82 | 3.90 | 23.50 |
| 23.26 | 3.83 | 50.40 |
| 24.01 | 3.71 | 57.60 |
| 24.73 | 3.60 | 24.10 |
| 25.62 | 3.48 | 9.90 |
| 25.99 | 3.43 | 8.00 |
| 26.37 | 3.38 | 4.60 |
| 27.37 | 3.26 | 13.50 |
| 27.98 | 3.19 | 23.20 |
| 28.62 | 3.12 | 15.70 |
| 30.20 | 2.96 | 19.00 |
| 30.71 | 3.41 | 17.30 |
| 31.29 | 2.86 | 32.40 |
| 31.40 | 2.85 | 33.30 |
| 31.73 | 2.82 | 25.10 |
| 32.71 | 2.74 | 12.40 |
| 33.84 | 2.65 | 9.70 |
| 34.55 | 2.60 | 10.20 |

* * * * *